US008736828B2

(12) United States Patent
Vertoprakhov et al.

(10) Patent No.: US 8,736,828 B2
(45) Date of Patent: May 27, 2014

(54) METHOD AND APPARATUS FOR INSPECTING OPHTHALMIC LENS

(71) Applicant: VisionXtreme Pte LTD, Singapore (SG)

(72) Inventors: Victor Vertoprakhov, Singapore (SG); Soon Wei Wong, Singapore (SG); Tian Poh Yew, Singapore (SG)

(73) Assignee: VisionXtreme Pte Ltd, Singapore (SG)

( * ) Notice: Subject to any disclaimer, the term of this patent is extended or adjusted under 35 U.S.C. 154(b) by 7 days.

(21) Appl. No.: 13/776,443

(22) Filed: Feb. 25, 2013

(65) Prior Publication Data

US 2013/0162984 A1    Jun. 27, 2013

Related U.S. Application Data

(63) Continuation of application No. 13/520,524, filed as application No. PCT/SG2011/000074 on Feb. 23, 2011, now abandoned.

(51) Int. Cl.
*G01B 9/00* (2006.01)
*G01N 21/00* (2006.01)
*G06K 9/00* (2006.01)

(52) U.S. Cl.
USPC .................. 356/124; 356/239.2; 382/141

(58) Field of Classification Search
None
See application file for complete search history.

(56) References Cited

U.S. PATENT DOCUMENTS

| | | | |
|---|---|---|---|
| 5,574,554 A * | 11/1996 | Su et al. ...................... 356/124 |
| 5,686,981 A | 11/1997 | Anan et al. |
| 6,765,661 B2 * | 7/2004 | Biel et al. ...................... 356/124 |
| 6,882,411 B2 * | 4/2005 | Dispenza et al. ............. 356/124 |
| 2002/0082476 A1 | 6/2002 | Takahashi et al. |
| 2002/0122172 A1 * | 9/2002 | Ross et al. ..................... 356/124 |
| 2002/0149745 A1 | 10/2002 | Fukuma et al. |
| 2003/0098951 A1 | 5/2003 | Hakamata |
| 2004/0189981 A1 * | 9/2004 | Ross et al. ..................... 356/124 |
| 2007/0206184 A1 | 9/2007 | Uto et al. |
| 2008/0204736 A1 | 8/2008 | Chikamatsu et al. |
| 2013/0169955 A1 * | 7/2013 | Vertoprakhov et al. ........ 356/124 |

OTHER PUBLICATIONS

International Search Report for Application Serial No. PCT/SG2011/000074, Korean Intellectual Property Office, Aug. 12, 2011, pp. 5.

* cited by examiner

*Primary Examiner* — Gordon J Stock, Jr.
(74) *Attorney, Agent, or Firm* — Axis Intellectual Capital Pte Ltd

(57) ABSTRACT

An embodiment of a system and a method for inspecting a contact lens is provided. The illumination system illuminates the center zone and the peripheral zone of the contact lens when it is inside a cavity between a male mold and a female mold. The imaging optical system has two channels to capture two images or a composite single image to inspect the entire contact lens. The imaging optical system of the first channel has its entrance pupil far away from the mold tool. The camera of the first channel is used to capture the image of the center zone of the contact lens. The image optical system of the second channel is located outside the mold tool but its entrance pupil is located inside the mold tool or outside but substantially close to it. This enables the camera of the second channel to capture the image of the peripheral zone of the contact lens.

18 Claims, 9 Drawing Sheets

METHOD AND APPARATUS FOR INSPECTING OPHTHALMIC LENS

PRIORITY CLAIM

The present application is Continuation of U.S. patent application Ser. No. 13/520,524, filed Jul. 3, 2012; which application is a national phase application filed pursuant to 35 USC §371 of International Patent Application Serial No. PCT/SG2011/000074, filed Feb. 23, 2011; all the foregoing applications are incorporated herein by reference in their entireties.

TECHNICAL FIELD

The embodiments herein relate to ophthalmic lenses and, more particularly, but not exclusively to inspection of ophthalmic lenses, for example, in an automated-lens manufacturing line.

BACKGROUND

Generally, ophthalmic lenses are manufactured on automated production lines, which include various production steps and inspection steps. In the process of manufacturing ophthalmic lenses commonly referred to as contact lenses, the lenses are inspected at various stages of its manufacture. Inspecting the lenses enables identification of defects, if any. Such inspection at different stages of manufacture not only enables removal of defective items before shipment to a customer, but also enables rectification of the process problems through analysis of the defective items, which in turn results in improvement in quality and also significant savings in terms of time and effort. One such stage at which the contact lenses are inspected is after the contact lens is cast-molded in molds. At this stage, the contact lens is inspected to identify existence of defects such as, bubbles in the polymer of clear and printed contact lens, print smear in the case of printed contact lens, in addition to any other defects encountered in a contact lens.

Colored or printed contact lens enhances the beauty of the eyes of the user. As the market volumes for such lenses are large, it is required to produce these lenses in large volumes using automated systems. In spite of high-production volumes, it is critical that quality is maintained as these contact lenses make physical contact with the eyes. A number of systems exist today that inspect the lenses after the cast-molding process. Traditional systems require one of the molds to be disengaged or removed to provide an open zone for an inspection system to be positioned above the lenses for capturing images of the complete lens. This process increases the time to inspect the finished product and it becomes difficult to differentiate whether defects existed before or after the disengagement of one of the molds.

Other prior-art systems exist that inspect the contact lens when it is within the mold assembly. Such systems include an illumination system, imaging optical system, and camera. In such prior-art systems, direct light rays illuminate the contact lens, and the light rays emerging from the contact lens are captured by the imaging optical system to generate an image of the contact lens. The entrance pupil of the image optical system, in prior-art systems, is located near or behind the lens of the image optical system and is far away from the mold case. The resulting image will allow inspection of only a portion (center zone) of the contact lens. The light emerging from a peripheral zone of the contact lens cannot reach the imaging optical system because a certain part of the case of the male mold blocks the light rays emerging from the peripheral zone.

SUMMARY

Therefore a need exists in the industry to clearly distinguish the defects that occur during the process of lens manufacturing and those defects that occur after the mold-disengagement process. Further, a need exists in the industry for a system that can perform inspection of the complete contact lens (center zone as well as peripheral zone) when the contact lens is disposed in the cavity between the two molds.

In view of the foregoing, an embodiment herein provides a method for inspecting an ophthalmic lens (hereinafter referred to as contact lens) when the contact lens is molded in the cavity of the mold assembly. The contact lens is inspected when the contact lens is disposed in a cavity between a male and a female mold of a mold assembly. The contact lens is inspected by illuminating it using an illumination system. The contact lens is illuminated by direct light rays as well as angular light rays reflected from the case of a female mold. A portion of each of the molds corresponding to the cavity between the male mold and the female mold is translucent or transparent, thereby allowing light to pass through them. The light rays emerging from the contact lens are collected using an imaging optical system. The lens system is designed such that, the entrance pupil of the imaging optical system is located inside the case of the male mold or located outside but substantially close to the case of the male mold, thereby enabling capturing of light rays emerging from the peripheral zone of the contact lens.

Further, the light collected by the imaging optical system is used by a camera to capture the image of the contact lens. It may be noted that, in some cases the female mold has a profile that blocks light from the illumination system. In such a case, the image captured by the camera will have a dark ring in the center zone making this zone unusable for inspection. In such images, the captured image is used to inspect only the defects in the peripheral zone of the contact lens.

In another embodiment, to overcome the dark ring zone that is caused in the first embodiment, the contact lens is illuminated by direct light rays and angular light rays. The light rays emerging from the contact lens are split into two channels using a beam splitter. The light that is split to travel in the first channel is collected by a first imaging optical system and the light that is split to travel in the second channel is collected by a second imaging optical system. The first channel imaging optical system is configured in such a way that the entrance pupil is located close to the lens. The light rays emerging from the center zone of the contact lens enter the imaging optical system of the first channel and the camera of the first channel imaging optical system captures an image, which is used to inspect the center zone of the contact lens. The second channel imaging optical system is designed such that the entrance pupil of the lens of the imaging optical system is located inside the case of the male mold or located outside but substantially close to the case of the male mold, thereby enabling capturing of light rays emerging from the peripheral zone of the contact lens. The camera of the second channel imaging optical system captures an image, which is used to inspect the peripheral zone of the contact lens.

In another embodiment, the contact lens is illuminated by direct light rays as well as angular light rays. The light rays emerging from the contact lens are collected using an imaging optical system. The imaging optical system of this embodiment is conceptually similar to the previous embodiment;

however in this embodiment, a single camera and a single image are used to inspect the entire contact lens. The light rays collected by the imaging optical system are used to generate intermediate images of the center zone and the peripheral zone of the contact lens. Further, the image optical system merges the two intermediate images into a single image, which is captured by a single camera, thereby enabling identification of defects in the center zone as well as the peripheral zone of the contact lens.

Embodiments further disclose a system for inspecting a contact lens when the contact lens is disposed in a cavity between a male mold and a female mold. The system includes an illumination system, an imaging optical system and at least one camera. The illumination system is configured to illuminate the contact lens with direct light rays as well as angular light rays reflected from the case of the female mold. Further, the imaging optical system is configured to capture light rays emerging from all zones of the contact lens. Further, the at least one camera is configured to capture image of the contact lens using the light captured by the imaging optical system.

These and other aspects of the embodiments herein will be better appreciated and understood when considered in conjunction with the following description and the accompanying drawings.

BRIEF DESCRIPTION OF THE DRAWINGS

The embodiments herein will be better understood from the following detailed description with reference to the drawings, in which.

DETAILED DESCRIPTION

Figure 1:
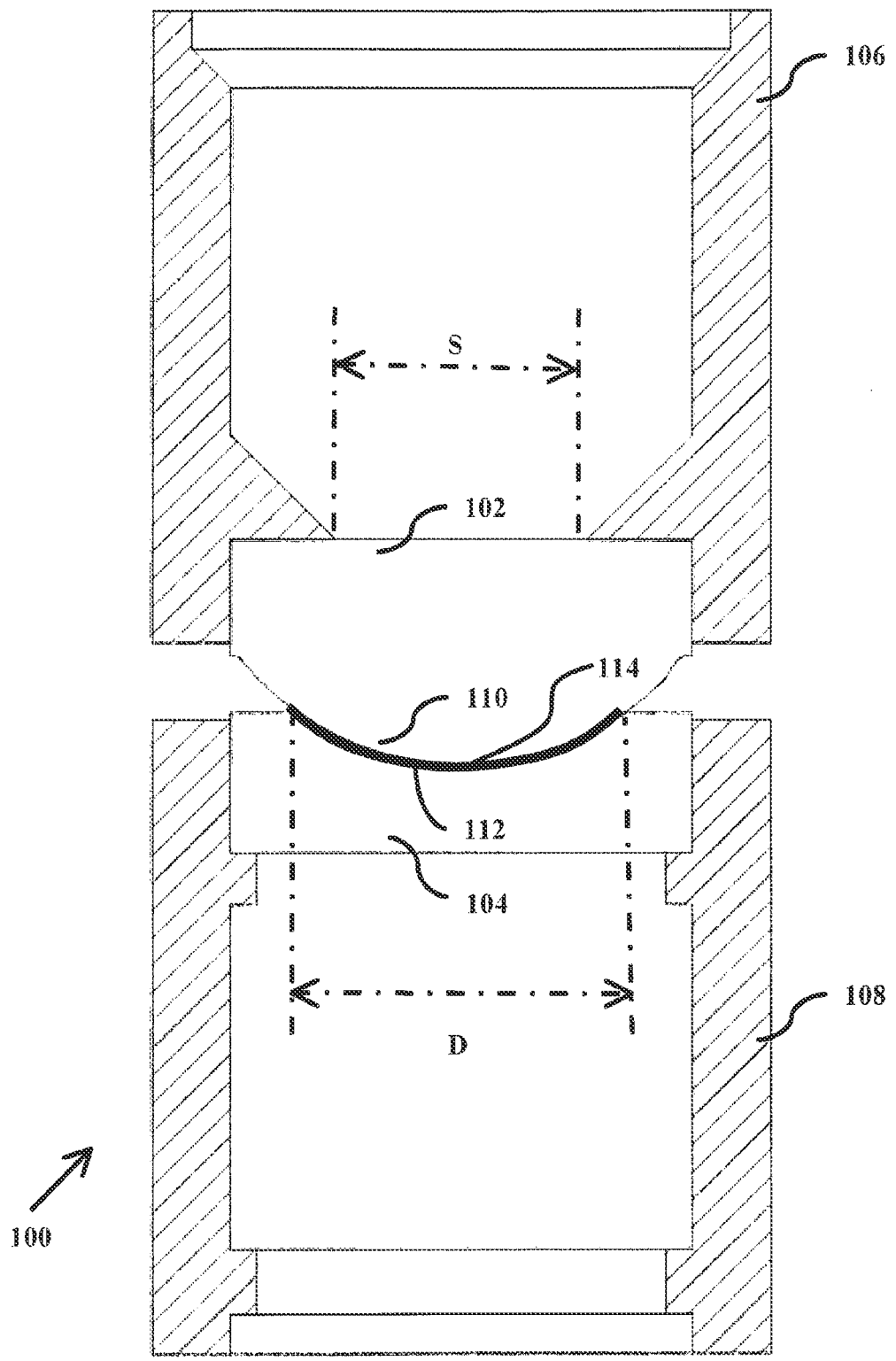
FIG. 1 illustrates a mold assembly 100 for molding contact lens 114, in accordance with an embodiment.

The embodiments herein and the various features and advantages thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein disclose method and system for inspecting an ophthalmic lens (herein after referred to as contact lens) when the contact lens is disposed in a cavity between a male and female mold of a mold assembly. Referring now to the drawings, and more particularly to FIGS. 1 through 10, where similar reference characters denote corresponding features consistently throughout the figures, there are shown embodiments.

The system for inspecting a contact lens when the contact lens is still within a mold assembly includes an illumination system, an imaging optical system, and at least one camera. In an embodiment, the illumination system is configured to illuminate the contact lens using direct light rays and angular light rays. Further, the optical imaging system is configured to receive the light rays emerging from the contact lens. Further, the camera is configured to capture an image of the contact lens using the light received by the imaging optical system.

FIG. 1 illustrates a mold assembly 100 for manufacturing a contact lens 114. The assembly 100 includes a male mold 102 and a female mold 104, which form a mold cavity when they are in an engaging position. A portion of each of the molds corresponding to the cavity is translucent or transparent, so as to allow light to pass through it. The male mold 102 is coupled with a case 106, and the female mold 104 is coupled with a case 108. Further, the male mold 102 has a curved surface 110, and the female mold 104 has a curved surface 112, such that, when the mold assembly 100 is in an engaging position, as shown in FIG. 1, the curved surfaces 110 and 112 define the mold cavity corresponding to the shape of the contact lens 114 to be molded. The contact lens 114 is manufactured by molding contact-lens material in the cavity. Further, the mold assembly 100 can assume a disengaging position (not shown in the figure), enabling removal of the contact lens 114 out of the mold assembly 100.

Figure 2:
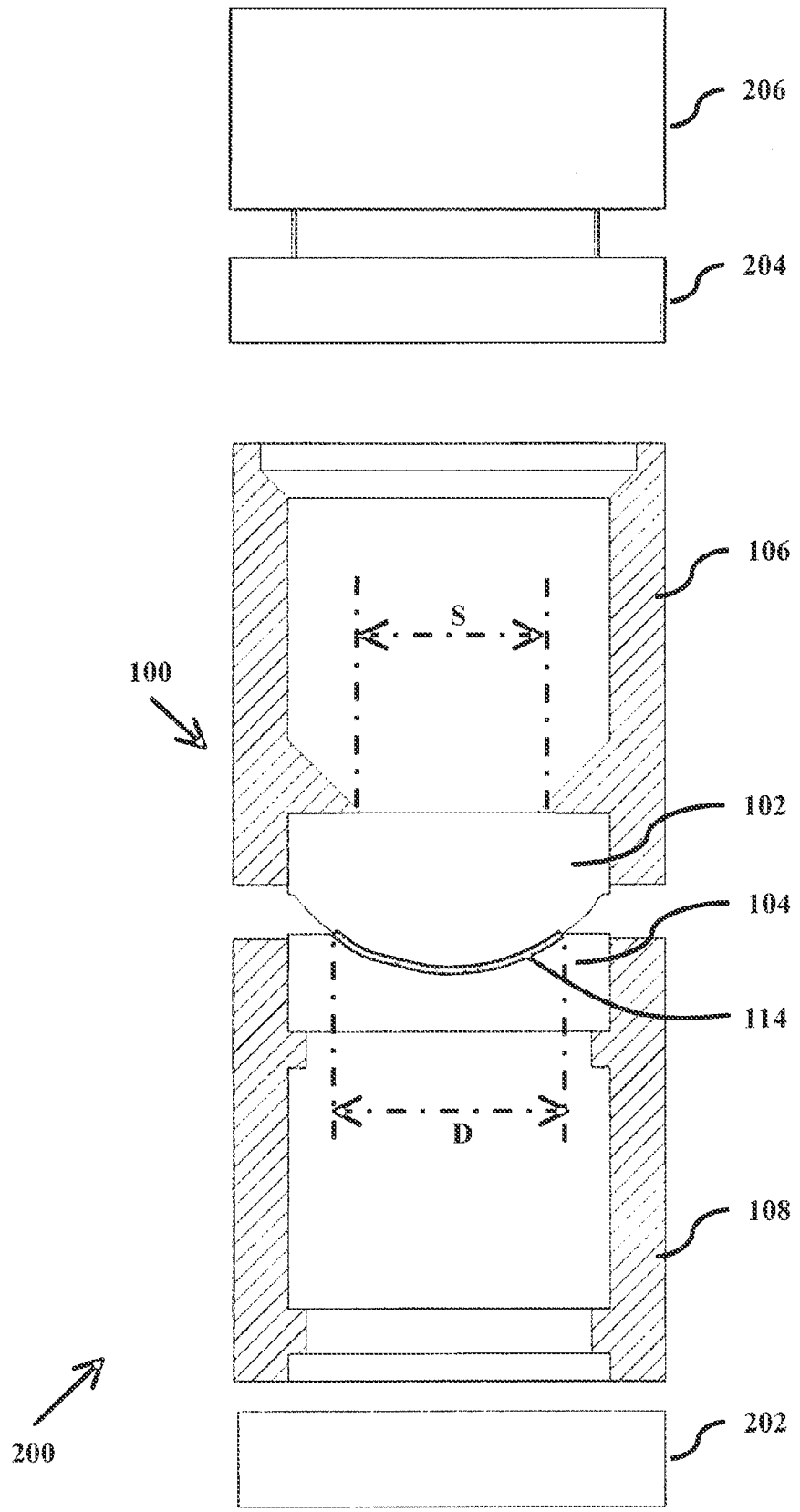
FIG. 2 illustrates a system 200 for inspecting contact lens 114 when it is inside the mold assembly 100, in accordance with an embodiment.

FIG. 2 illustrates a system 200 for inspecting the contact lens 114 when the contact lens 114 is disposed in a cavity between the male mold 102 and female mold 104, in accordance with an embodiment.

The system 200 includes an illumination system 202, an imaging optical system 204, and a camera 206. In an embodiment, the illumination system 202 is configured to illuminate the contact lens 114. The illumination system 202 illuminates the contact lens 114 by direct light rays as well as angular light rays reflected from the case of the female mold 108. In this specification, the embodiments are described by considering that light rays are emitted into the case 108 of the female mold 104. Further, the illumination system 202 is configured to emit direct light rays and angular light rays. Further, the imaging optical system 204 is configured to receive light rays emerging from the contact lens 114. Further, the camera 206 is configured to use the light received by the imaging optical system 204 to capture an image of the contact lens 114. In an embodiment, the camera 206 is a digital camera, which is configured to capture images of the contact lens 114.

In FIG. 2 the illumination system 202 is located on a first side of the mold assembly 100, such that the illumination system 202 is proximate to the female mold 104 as compared to the male mold 102. The illumination system 202 is positioned in such a way that light from the illumination system 202 is directed towards the contact lens 114. In an embodiment, the illumination system 202 is positioned along the longitudinal axis of the mold assembly 100. While the illumination system 202 is located on the first side of the mold assembly 100, the imaging optical system 204 and the camera 206 are located on the second side of the mold assembly 100. The imaging optical system 204 is located in between the camera 206 and the mold assembly 100.

Figure 3:
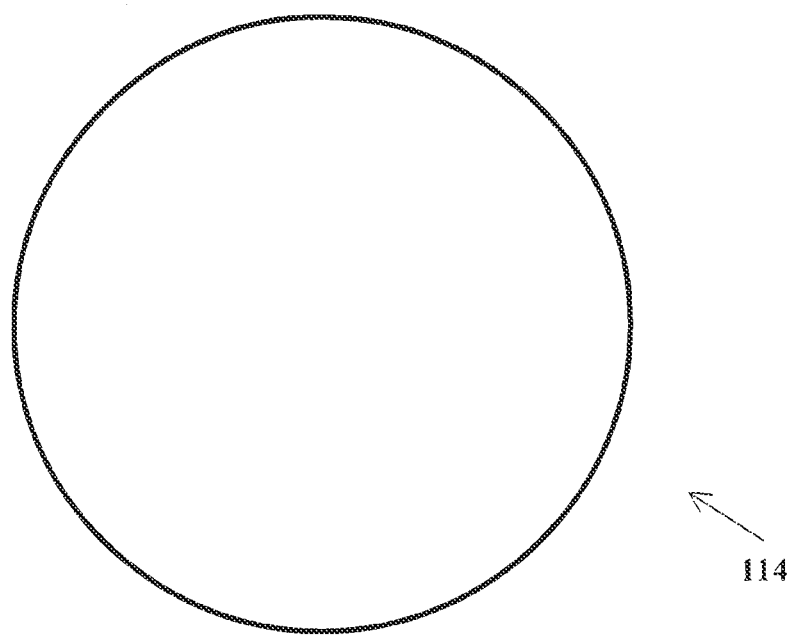
FIG. 3 illustrates complete zone of the contact lens 114 that needs to be inspected, in accordance with an embodiment.
Figure 4:
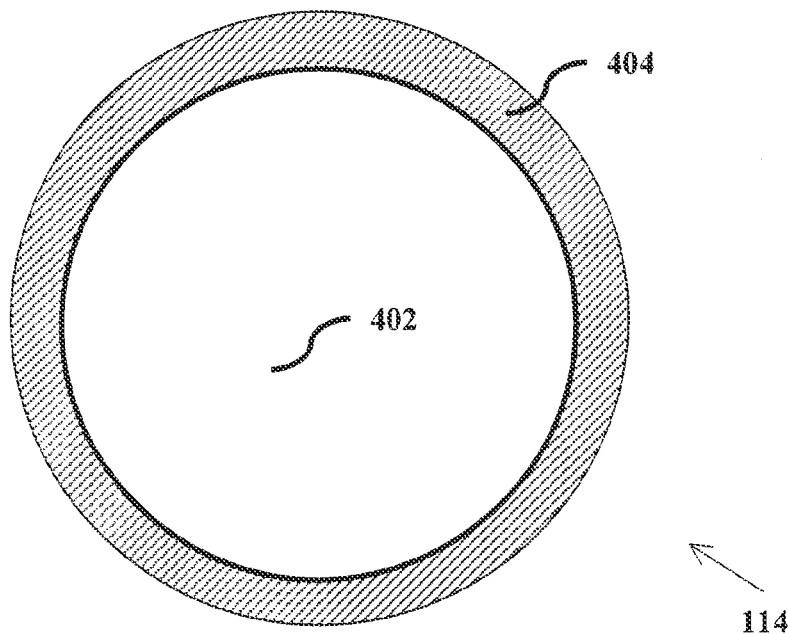
FIG. 4 illustrates the center zone 402 and periphery zone 404 of the contact lens 114, in accordance with an embodiment.

FIG. 3 illustrates the complete contact lens 114, an image of which is supposed to be captured to perform 100% inspection of the lens 114. Further, FIG. 4 is the same as FIG. 3 with the difference that the zone to be inspected is divided into a center zone (non-shaded zone) 402 and a peripheral zone (shaded zone) 404. In the case of prior-art systems used for inspecting a contact lens disposed in the cavity of the mold assembly, the image captured is not suitable for inspecting the peripheral zone 404. Hereinafter, a first portion of the contact lens 114 corresponding to the non-shaded zone 402 illustrated in FIG. 4 will be referred to as the center zone and a second portion of the contact lens 114 corresponding to the shaded zone 404 that is illustrated in FIG. 4 will to referred to as the peripheral zone. The shaded zone 404 is not captured because the case 106 (see FIG. 2) of the male mold 102 has inner size S smaller than the size of the contact lens D. Thus the case 106 of the male mold 102 blocks light from a portion of the contact lens. Furthermore, the entrance pupil of the lens of the image optical system of prior-art systems is located near or behind the imaging optical system, which is far away from the mold. Hence, the portion of the contact lens corresponding to the shaded zone 404 (FIG. 4) cannot be inspected by prior-art systems.

In an embodiment, the contact lens 114 is inspected when the mold assembly 100 is in the engaging position, which means that the contact lens 114 is disposed in a cavity between the male mold 102 and female mold 104 (see FIG. 2). The illumination system 202 illuminates the contact lens 114 by direct light rays as well as angular light rays reflected from the case of the female mold.

Figure 5:
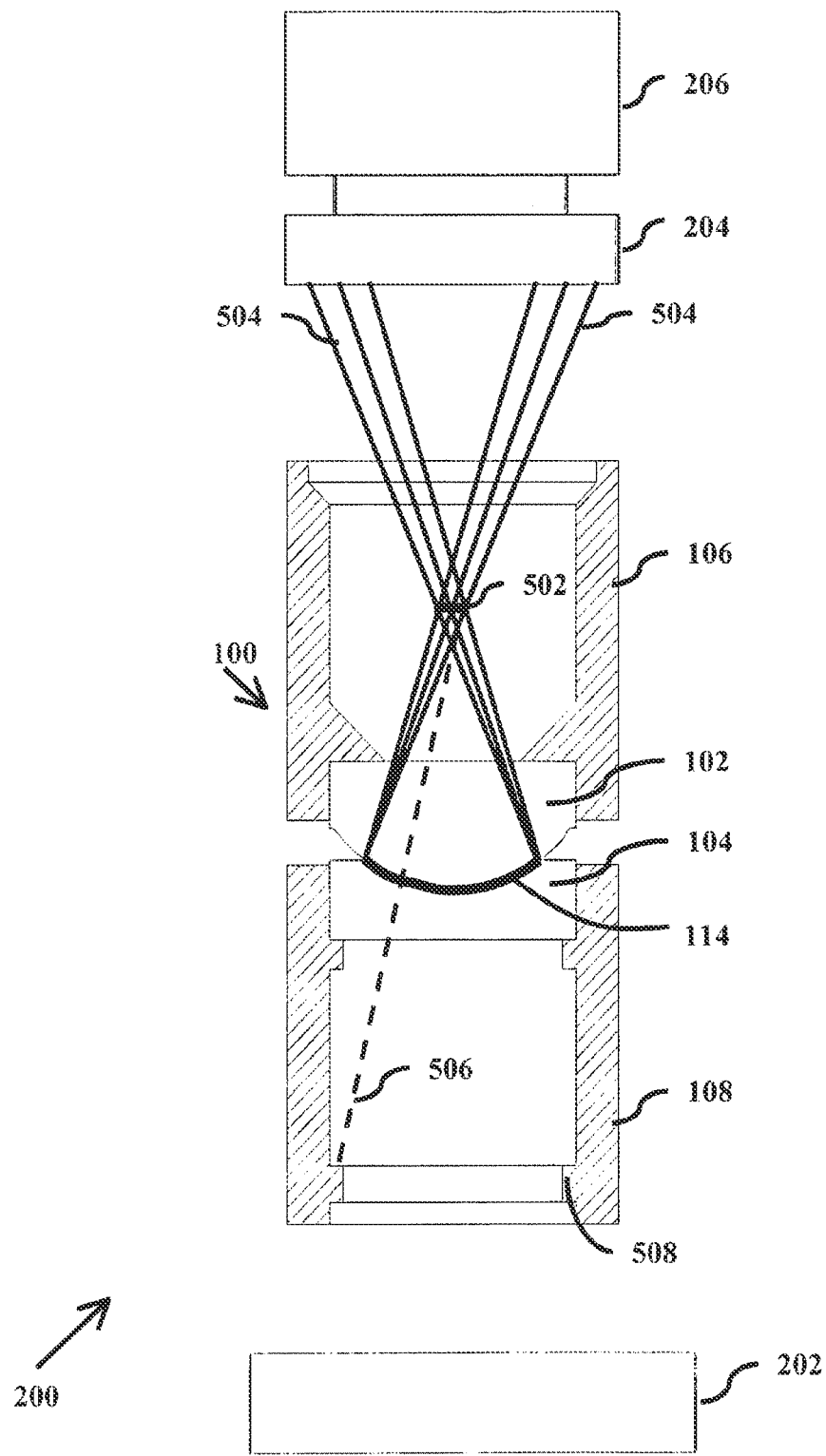
FIG. 5 illustrates the system 200 in which light rays 504 emerging from the peripheral zone of the contact lens 114 are depicted, in accordance with an embodiment.

FIG. 5 illustrates the system 200 in which light rays 504 emerging from the peripheral zone of the contact lens 114 are depicted, in accordance with an embodiment. The light rays 504 emerging from the peripheral zone of the contact lens pass through the entrance pupil 502 of the imaging optical system 204. The entrance pupil 502 of the imaging optical system 204 is located inside the case 106 of the male mold or outside, but substantially close to, the case of the male mold 106. The imaging optical system is placed far away from the case of the male mold 106. Locating the entrance pupil 502 inside the case 106 of the male mold or outside, but substantially close to, the case of the male mold 106 enables capturing of light rays emerging from the peripheral zone of the contact lens 114.

The camera 206 uses the light entering the imaging optical system 204 to capture an image, which will later be processed to identify the existence of defects (if any such defects are present) in the peripheral zone 404 of the contact lens 114 when the contact lens 114 is still inside a mold.

Figure 6:
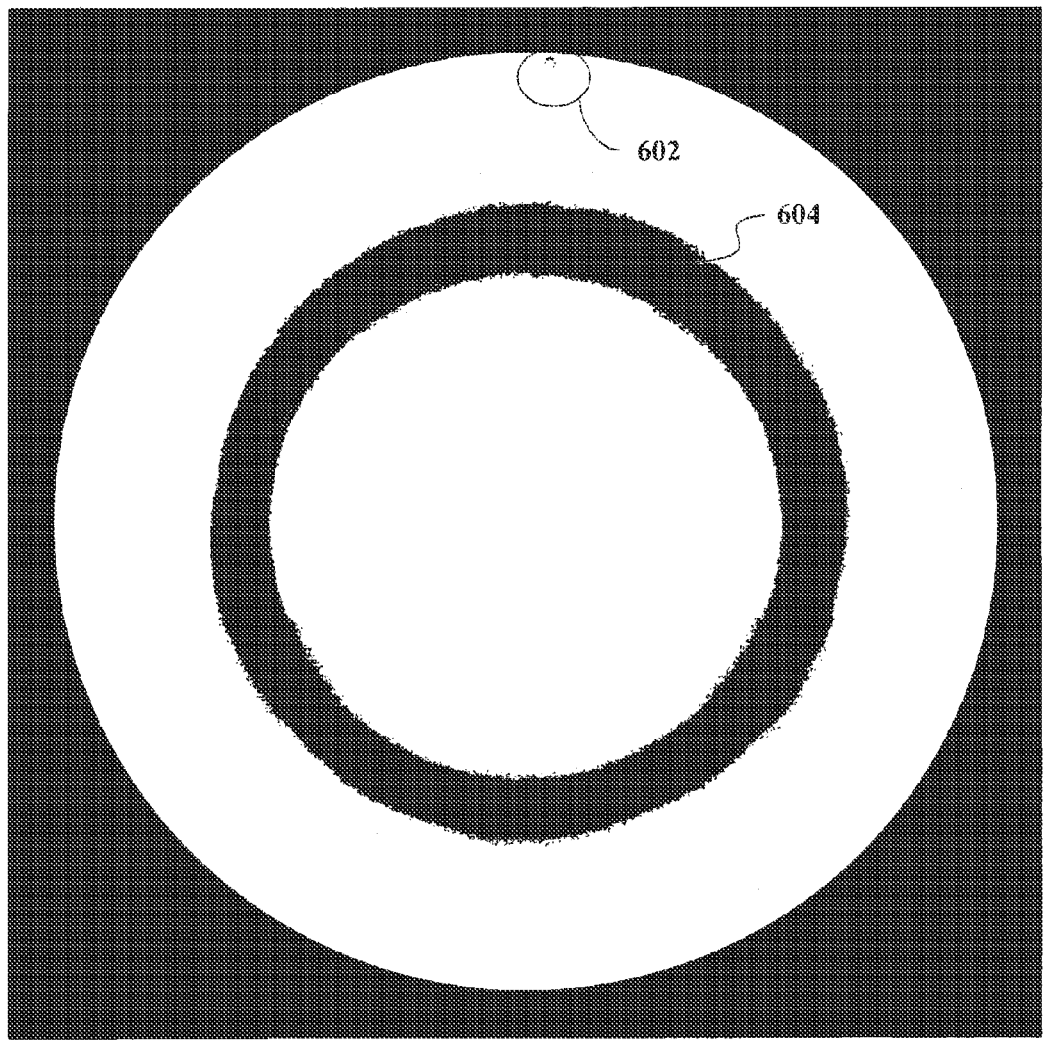
FIG. 6 illustrates an image of the contact lens 114 captured using the system 200 in which a bubble defect in the peripheral zone of the contact lens 114 is visible, in accordance with an embodiment.

FIG. 6 illustrates an image 600 of the contact lens 114 captured using the system 200, in accordance with an embodiment. In this image, a bubble defect 602 is present in the peripheral zone. The illumination system 202 (see FIG. 5) illuminates the contact lens 114 by direct light rays as well as angular light rays reflected from the case of the female mold. The imaging optical system 204 utilizes the angular light rays emerging from the contact lens 114 to produce the image in FIG. 6, which is captured by the camera 206. It is to be noted that the case of female mold 106 has a profile 508 that blocks a portion of the light from the illumination system 202, and there is no reflected light from this zone of the case of female mold 104. The dark ring 604 (FIG. 6) in the captured image 600 corresponds to this profile 508. In the FIG. 5, line 506 illustrates a virtual ray corresponding to the profile 508 that is responsible for the dark ring 604 in the image. This dark ring is located in the center zone of the contact lens 114. Hence the resulting image can only be used for inspecting the peripheral zone of the contact lens 114.

In an embodiment, the illumination system 202 is configured to illuminate the center zone using the direct rays as well as angular rays, and the imaging optical system is configured to capture another image, which is used to inspect the center zone of the contact lens. Capturing of 2 images enables 100% inspection of the contact lens.

Figure 7:
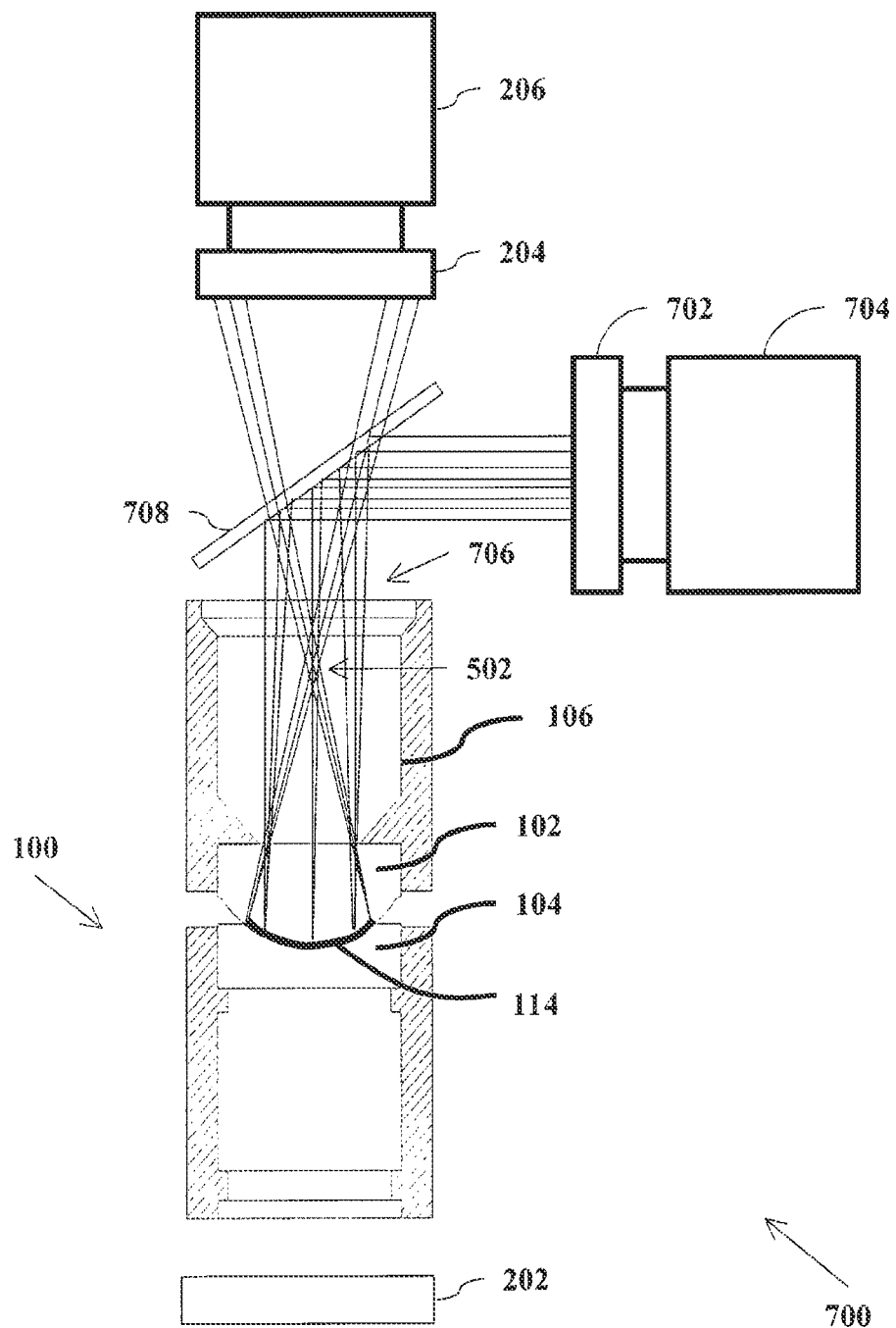
FIG. 7 illustrates a two-channel, two-camera system 700 for inspecting contact lens 114, in accordance with an embodiment.

FIG. 7 illustrates a two-channel, two-camera system 700 for inspecting contact lens 114 while inside a mold assembly 100, in accordance with an embodiment. It may be noted that system 700 illustrated in FIG. 7 has some elements, which are common to the elements of system 200, and such common elements have been assigned the same reference number. In system 700, the imaging optical system includes a beam splitter 708, a first channel imaging optical system 702, and a second channel imaging optical system 204. Further, the system 700 includes a first camera 704 associated with the first channel imaging optical system 702 and a second camera 206 associated with the second channel imaging optical system 204. The beam splitter 708 is configured to split light rays 706 emerging from the contact lens 114 into first channel and second channel. Further, entrance pupil 502 of the second imaging optical system 204 is located inside the case of the male mold 106 or located outside, but substantially close to, the case of the male mold 106. The second channel imaging optical system 204 is located far away from the case 106. Locating the entrance pupil 502 inside the case of the male mold 106 or locating it outside but substantially close to the case of the male mold 106 enables capturing of light rays emerging from the periphery zone of the contact lens 114. The light rays in the second channel that enter the second channel imaging optical system 204 and second camera 206 enable capturing of the image as illustrated in FIG. 6. This image is used to inspect the peripheral zone of the contact lens 114.

Figure 8:
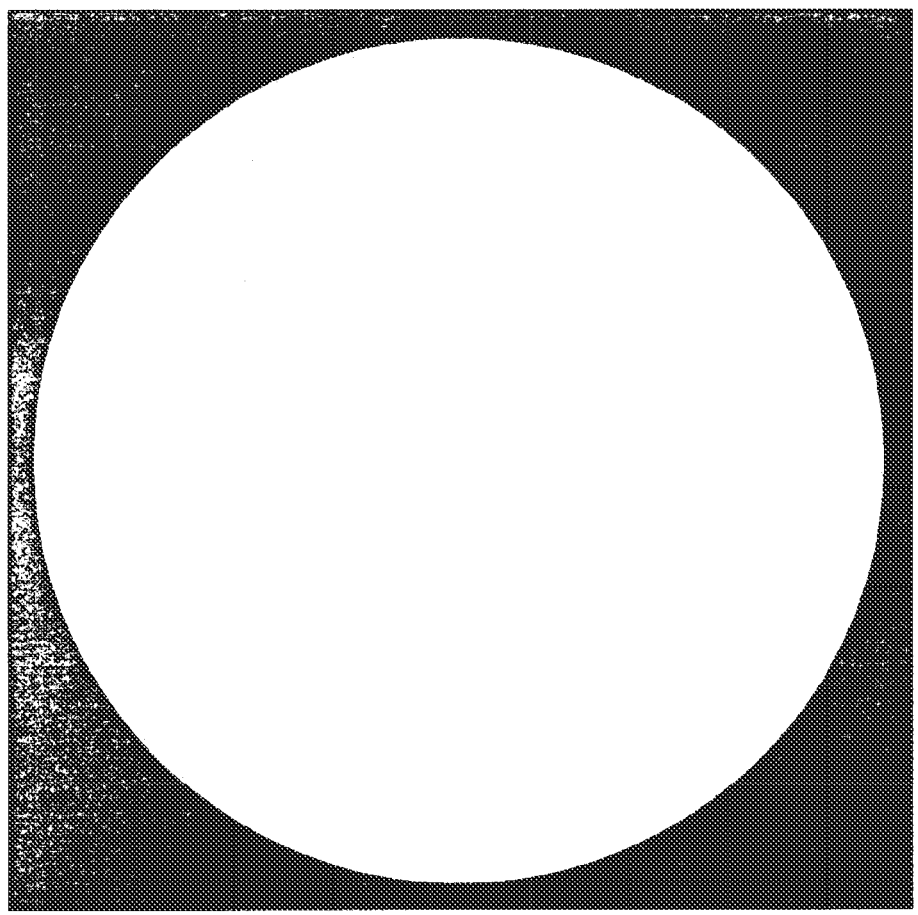
FIG. 8 illustrates the image captured by the camera of the first channel of the two-channel imaging optical system, which is used to inspect a center zone of the contact lens 114, in accordance with an embodiment.

Further, the light rays of the first channel that enter the first channel imaging optical system 702 and first camera 704 enable capturing of another image as illustrated in FIG. 8. The first channel imaging optical system 702 is a standard imaging optical system similar to prior-art systems and has its entrance pupil located far away from the case of the male mold 106.

By analyzing the two images, defects in both the center zone as well as the peripheral zone can be detected, resulting in 100% inspection of the complete lens 114 when it is still inside a mold assembly 100. It also enables the use of two different optical magnifications for each channel. Additionally the system enables use of two different-resolution cameras for each channel. This flexibility allows enhancement in performance of this embodiment.

Figure 9:
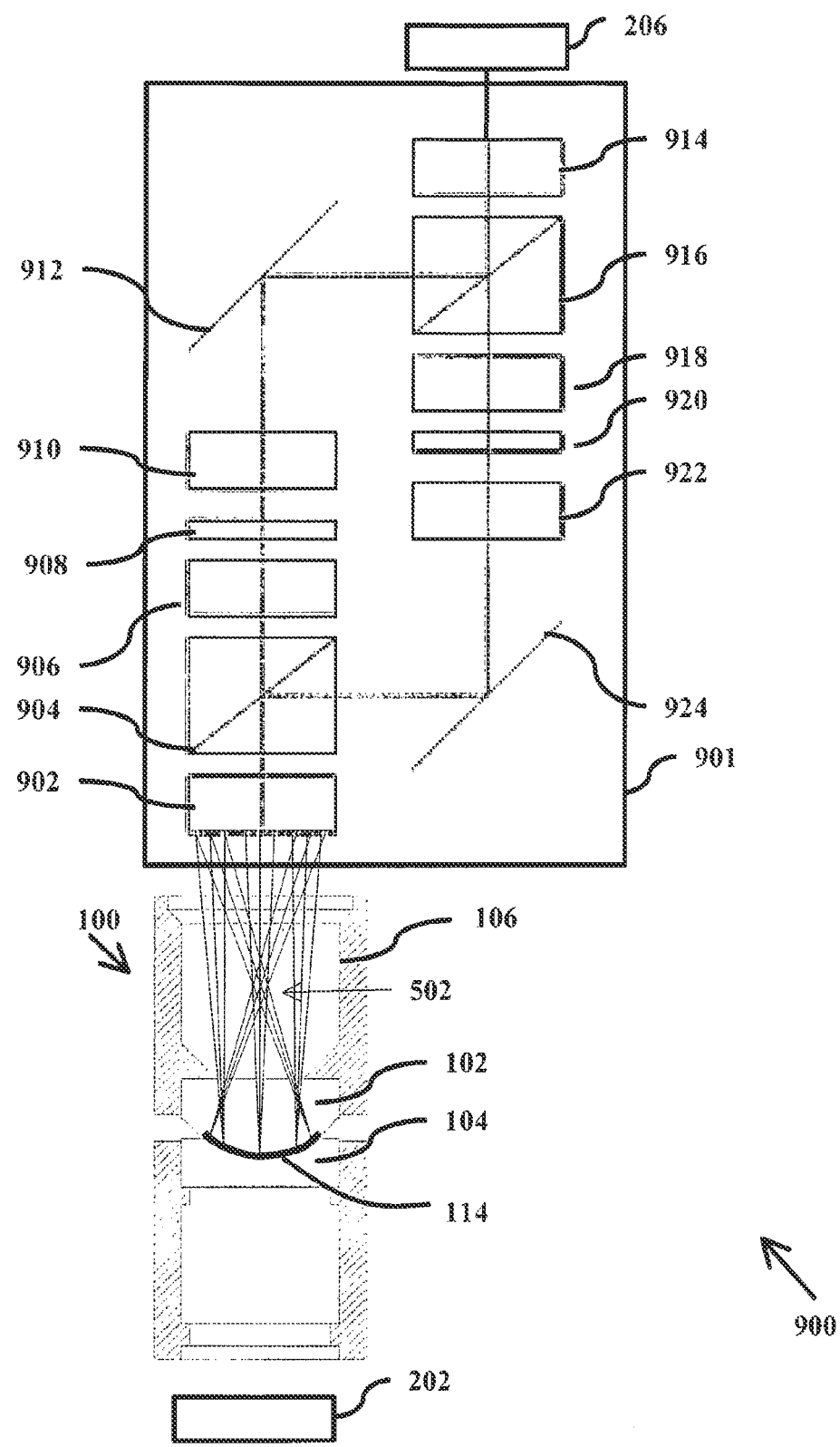
FIG. 9 illustrates a two-channel, single-camera system 900 for inspecting the entire contact lens 114, in accordance with an embodiment.
Figure 10:
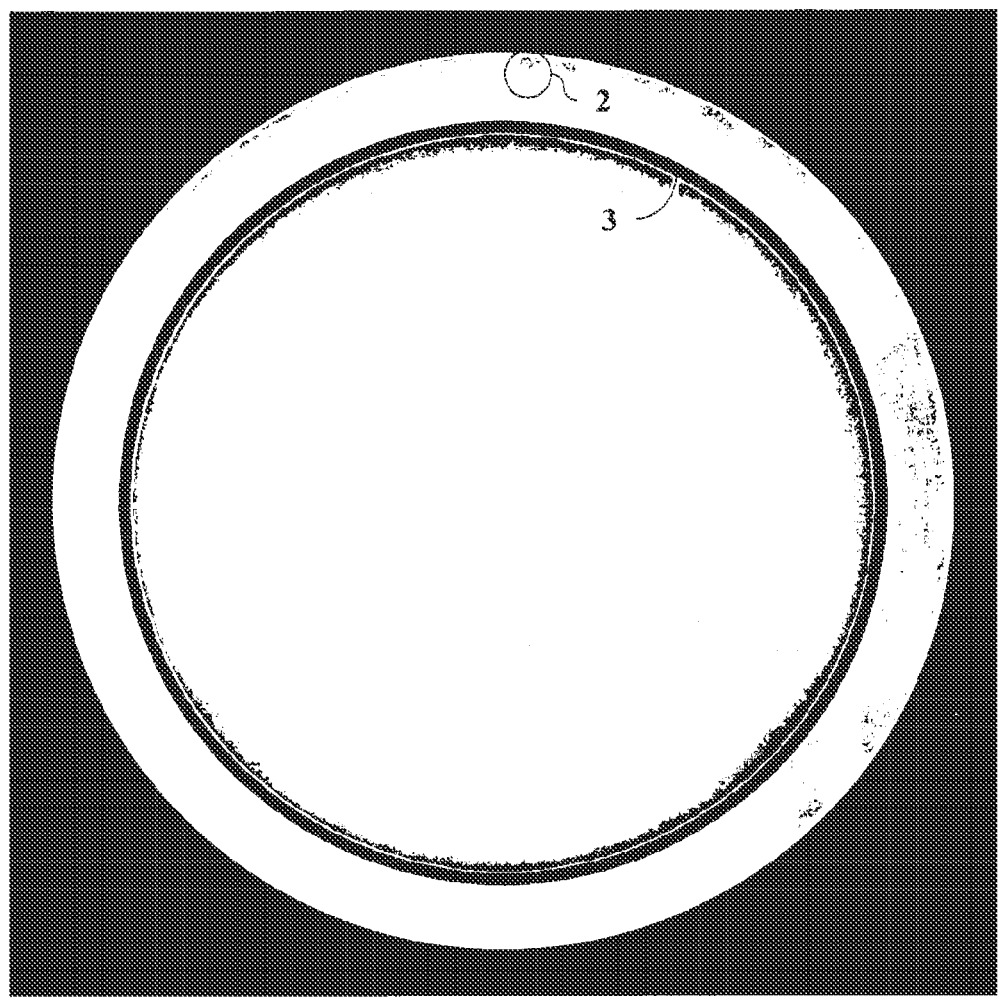
FIG. 10 illustrates an image of the entire contact lens 114 captured using a system 900, in accordance with an embodiment.

Further, FIG. 9 illustrates a two-channel, single-camera system 900 for inspecting a contact lens 114, which is inside a mold assembly 100, in accordance with an embodiment. It may be noted that system 900 illustrated in FIG. 9 has some elements that are common to the elements of system 200 and system 700, and such common elements have been assigned the same reference number. The imaging optical system 901 of system 900 includes groups of lens elements 902, 906, 910, 914, 918 and 922, beam splitters 904 and 916, a first field stop 908, a second field stop 920, and mirrors 912 and 924.

The imaging optical system 901 has two channels. The first channel includes items 906, 908, 910 and 912 and the second channel includes items 918, 920, 922 and 924. There are a few common items 902, 904, 914 and 916 for both the optical channels. The positions of the entrance pupils of the two optical channels may be different. The entrance pupil of the first channel may be located far away from the molds. In contrast, the entrance pupil 502 of the second channel may be located inside the case 106 of the male mold 102 or outside but substantially close to it. The image optical system 901 is located far away from the mold.

Placing the entrance pupil 502 inside the case 106 of the male mold 102 or outside, but substantially close to it, enables the second channel of the imaging optical system 901 to capture light rays emerging from the peripheral zone of the contact lens 114.

Light from the contact lens 114 reaches the beam splitter 904 through the groups of lens elements 902. The beam splitter splits the light rays into two channels.

The two channels generate two intermediate images and merge these images into a single image that is captured by the camera 206, which is attached to the optical system 901. The first intermediate image is an image of the center zone of the contact lens 114, and the second intermediate image is an image of the peripheral zone of the contact lens 114. The first field stop 908 is equal to the diameter of the center zone of the first intermediate image. Further, the second field stop 920 is a ring-type stop in which the outer diameter of the ring is equal to the outer diameter of the peripheral zone of the image and the inner diameter of the ring is equal to the inner diameter of the peripheral zone of the second intermediate image. Further, it may be noted that the center disk of the second field stop 920 is opaque. The two intermediate images filtered by field stops 908 and 920 are further imaged and merged into a single image as displayed in FIG. 10. The optical magnifications of the intermediate images may be different. In the image illustrated in FIG. 10, a black ring 3 corresponding to the edge of the center opaque circle of the $2^{nd}$ field stop is present. The width of black ring 3 may vary and may also be zero (non existence of the black ring) depending upon the optics design. Further, in an embodiment, it is possible to adjust the optical magnifications of the intermediate images and the optical magnifications of the further image to provide overlapping of the images of the center and peripheral zone. Overlapping of intermediate images results in overlapping of a small zone of the contact lens near the boundary of the center zone and peripheral zone of the contact lens 114. The final combined image is used to inspect both the center zone and the peripheral zone of the contact lens 114. This results in 100% inspection of the complete lens when it is still inside a mold.

The embodiments disclosed herein can be implemented through at least one software program running on at least one hardware device on a network.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein may have been described in terms of preferred embodiments, those skilled in the art will recognize that the embodiments herein can be practiced with modification within the spirit and scope of this disclosure.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated.

What is claimed is:

1. A method for inspecting a contact lens for defects when the contact lens is disposed in a cavity between a male mold and a female mold, the method comprising:
    illuminating the contact lens using direct light rays and angular light rays;
    capturing light rays emerging from the contact lens by a two-channel imaging optical system;
    configuring a first channel of the two-channel imaging optical system to capture the light rays emerging from a center zone of the contact lens;
    configuring a second channel of the two-channel imaging optical system to have an entrance pupil in a different position than an entrance pupil of the first channel of the two-channel imaging optical system, to capture the light rays emerging from a peripheral zone of the contact lens;
    capturing individual images using light rays entering each of the two channels of the two-channel imaging optical system, or capturing a single composite image from the two-channel imaging optical system; and
    processing the two images or the single composite image to detect defects in the contact lens.

2. The method according to claim 1, wherein illuminating the contact lens using angular light rays comprises, projecting light rays at an angle into an inner surface of the case of the female mold and using reflected light rays to illuminate the contact lens.

3. The method according to claim 1, wherein capturing the light emerging from the contact lens comprises, splitting light rays emerging from the contact lens into a first channel and a second channel.

4. The method according to claim 1, wherein capturing individual images from each of the two channels comprises, capturing image using light rays entering the first channel to inspect the center zone of the contact lens, and, capturing image using light rays entering the second channel to inspect the peripheral zone of the contact lens.

5. The method according to claim 1, wherein capturing a single composite image comprises, imaging two intermediate images from the two channels and then merging the two intermediate images into a single image for inspecting both the center zone and peripheral zone of the contact lens.

6. The method according to claim 1, wherein an area of the contact lens to be inspected is divided into a peripheral zone and a central zone.

7. A system for inspecting a contact lens for defects when the contact lens is disposed in a cavity between a male mold and a female mold, the system comprising:
    an illumination system configured to illuminate the contact lens disposed between the male and female molds by emitting direct and angular light rays into a case of the female or male mold;
    a two-channel imaging optical system comprising:
        a first channel imaging optical system configured to capture the light rays emerging from a center zone of the contact lens;

a second channel imaging optical system configured to have an entrance pupil in a different position than an entrance pupil of the first channel of the two-channel imaging optical system, to capture the light rays emerging from a peripheral zone of the contact lens;

two cameras for capturing individual images from each of the two channels of the two-channel imaging optical system, or a single camera for capturing a single composite image from the two-channel imaging optical system; and an image processing system for analyzing the images or image to detect defects in the contact lens.

8. The system according to claim 7, wherein the illumination system configured to illuminate the contact lens using angular light rays comprises, projecting light rays at an angle into an inner surface of the case of the female mold and using reflected light rays to illuminate the contact lens.

9. The system according to claim 7, wherein the two-channel imaging optical system is configured to split light emerging from the contact lens into a first channel and a second channel.

10. The system according to claim 7, wherein use of single camera comprises, a single camera to capture a composite image resulting from merger of two intermediate images corresponding to the two channels.

11. The system according to claim 7, wherein the male mold and the female mold form a mold cavity when the male and female mold are in an engaging position, a portion of each of the male mold and female mold corresponding to the cavity is translucent or transparent to allow light to pass through the portions.

12. The system according to claim 7, wherein each of the male and female mold is coupled with a case.

13. The system according to claim 7, wherein the first channel imaging optical system has an entrance pupil located far away from the case of the male mold.

14. The system according to claim 7, wherein use of two cameras comprises, a first camera to capture an image using the light rays entering the first channel to inspect the center zone of the contact lens, and a second camera to capture an image using the light rays entering the second channel to inspect the peripheral zone of the contact lens.

15. The system according to claim 7, wherein the first channel imaging optical system generates a first intermediate image, the first intermediate image being an image of the center zone of the contact lens; and the second channel imaging optical system generates a second intermediate image, the second intermediate image being an image of the peripheral zone of the contact lens.

16. The system according to claim 14, wherein each channel of two-channel imaging optical system uses a different camera of different optical resolution.

17. The system according to claim 15, wherein each channel of the two-channel imaging optical system comprises at least two field stops to filter the first and second intermediate images, wherein a first field stop used in the first channel equals the diameter of the center zone of the first intermediate image; and wherein a second field stop is a ring-type stop in which the outer diameter of the ring is equal to the outer diameter of the peripheral zone of the second intermediate image and the inner diameter of the ring is equal to the inner diameter of the peripheral zone of the second intermediate image.

18. The system according to claim 15, wherein the center zone of first intermediate images is surrounded by a black ring, and wherein the optical magnifications of the first and second intermediate images can be adjusted so that the overlapping of the first and second intermediate images can vary a width of the black ring or altogether eliminate the black ring to form a whole image of the contact lens for inspection.

\* \* \* \* \*